(12) United States Patent
Blair

(10) Patent No.: US 7,384,797 B1
(45) Date of Patent: Jun. 10, 2008

(54) RESONANT OPTICAL CAVITIES FOR HIGH-SENSITIVITY HIGH-THROUGHPUT BIOLOGICAL SENSORS AND METHODS

(75) Inventor: Steven M. Blair, SLC, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 836 days.

(21) Appl. No.: 10/089,497

(22) PCT Filed: Oct. 12, 2000

(86) PCT No.: PCT/US00/41138

§ 371 (c)(1),
(2), (4) Date: Aug. 21, 2002

(87) PCT Pub. No.: WO01/40757

PCT Pub. Date: Jun. 7, 2001

(51) Int. Cl.
*G01N 33/551* (2006.01)
*G01N 33/552* (2006.01)

(52) U.S. Cl. ............ 436/524; 385/12; 422/82.11; 435/287.1; 435/287.2; 435/288.7; 435/808; 436/164; 436/172; 436/527; 436/805

(58) Field of Classification Search ............ None
See application file for complete search history.

(56) References Cited

U.S. PATENT DOCUMENTS

| | | | |
|---|---|---|---|
| 4,857,273 A * | 8/1989 | Stewart | 422/82.11 |
| 5,244,636 A | 9/1993 | Walt et al. | |
| 5,340,715 A * | 8/1994 | Slovacek et al. | 435/6 |
| 5,344,784 A | 9/1994 | Attridge | |
| 5,347,784 A | 9/1994 | Crick et al. | |
| 5,434,663 A | 7/1995 | Maule | |
| 5,525,466 A | 6/1996 | Slovacek et al. | |
| 5,742,633 A * | 4/1998 | Stone et al. | 372/92 |
| 5,745,231 A | 4/1998 | Groger et al. | |

(Continued)

FOREIGN PATENT DOCUMENTS

WO WO 90/09476 8/1990

(Continued)

OTHER PUBLICATIONS

Dacil K-P S et al: Development of a Porous Silicon Based Biosensor, Advances in Microcrystalline and Nanocrystalline Semiconductors Symposium, vol. 536, Nov. 30, 1998, pp. 557-562, XP001104086.

(Continued)

*Primary Examiner*—Christopher L Chin
(74) *Attorney, Agent, or Firm*—Needle & Rosenberg, P.C.

(57) ABSTRACT

Biosensors including resonant optical cavities. The resonant optical cavities are shaped so as to generate whispering gallery modes, which increase the quality factors of the cavities and facilitate the detection of analytes in a sample with enhanced sensitivity. The sizes of the resonant optical cavities facilitate their use in biosensors that include arrays of sensing zones. Accordingly, the resonant optical cavities may be used in high-density sensing arrays that can be read in real-time and in parallel. Thus, the resonant optical cavities are useful for detecting small concentrations of samples in real-time and with high throughput. Different embodiments of the biosensors are also disclosed, as are methods for using the biosensors.

22 Claims, 6 Drawing Sheets

U.S. PATENT DOCUMENTS

| | | | |
|---|---|---|---|
| 5,766,957 A * | 6/1998 | Robinson et al. | 436/165 |
| 5,824,023 A | 10/1998 | Anderson | |
| 5,835,231 A * | 11/1998 | Pipino | 356/440 |
| 5,943,136 A | 8/1999 | Pipino et al. | |
| 6,020,207 A * | 2/2000 | Liu | 436/164 |
| 6,210,910 B1 | 4/2001 | Walt et al. | |
| 6,333,458 B1 | 12/2001 | Forrest et al. | |

FOREIGN PATENT DOCUMENTS

| | | |
|---|---|---|
| WO | WO90/09576 | 8/1990 |
| WO | WO91/06862 | 5/1991 |
| WO | WO92/21976 | 12/1992 |
| WO | WO93/14393 | 7/1993 |
| WO | WO94/25850 | 11/1994 |
| WO | WO97/35181 | 9/1997 |
| WO | WO 97 35181 A | 9/1997 |
| WO | WO99/37996 | 7/1999 |
| WO | WO 99/37996 | 7/1999 |
| WO | WO99/49937 | 10/1999 |

OTHER PUBLICATIONS

Heise H M et al.: "Attenuated total reflectio mid-infrared spectroscopy for clinical chemistry applications using silver halide fibers", vol. 51, No. 1-3, Aug. 31, 1998, pp. 84-91, Issn: 0925-4005, Figures 1, 3.

Pipino A C R: Ultrasensitive surface spectroscopy with a miniature optical resonator:, Physical Review Letters, New York, NY, US., vol. 83, No. 15, Oct. 11, 1999, pp. 3093-3096, XP002201594, ISSN: 0031-9007, Figure 1.

* cited by examiner

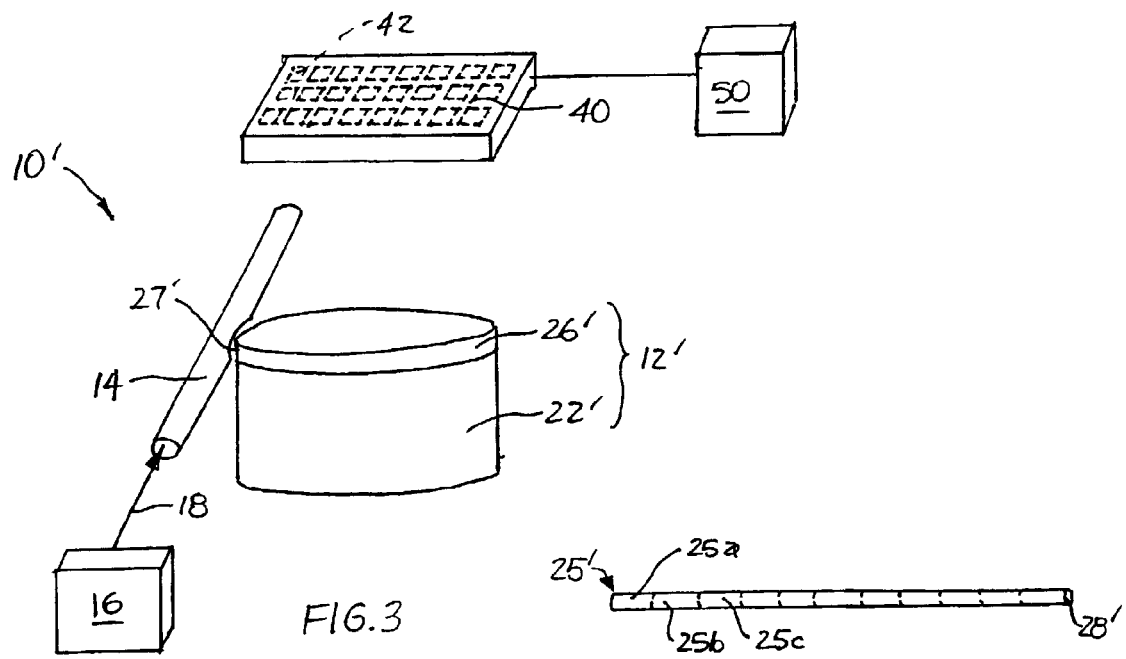
FIG. 3
FIG. 3A
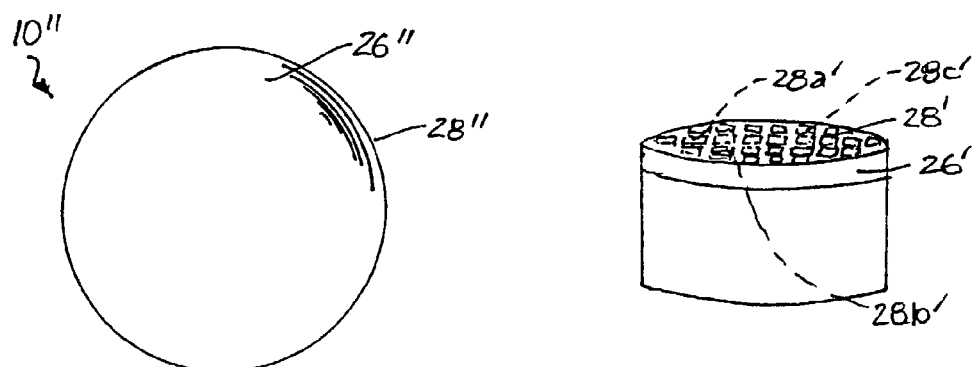
FIG. 4
FIG. 3B

RESONANT OPTICAL CAVITIES FOR HIGH-SENSITIVITY HIGH-THROUGHPUT BIOLOGICAL SENSORS AND METHODS

TECHNICAL FIELD

The present invention relates generally to optical biosensors and, particularly, to high throughput optical biosensors. More particularly, the optical biosensors of the present invention include structures that facilitate the use of whispering gallery modes for enhancing the sensitivity of the optical biosensors. The present invention also relates to methods for fabricating the optical biosensors, as well as to diagnostic methods that employ the optical biosensors.

BACKGROUND ART

Early and accurate diagnostics are crucial to the treatment of many medical disorders. High-throughput biosensing is an active and growing area of research for clinical applications in detecting antibodies, genes, drugs, peptides, cells, and other biological molecules of interest, as well as for sequencing DNA molecules.

Currently, the two major optical approaches to biosensing upon which research efforts are focused are the use of segmented evanescent waveguide biosensors and the use of the so-called "biochips", which basically include microfabricated substrates with capture biomolecules secured thereto.

Optical waveguides are often used in low sample concentration, high throughput immunoassays (IA) and molecular diagnostic assays (MDx). When a segmented waveguide is used, the waveguide is illuminated with one or more wavelengths of electromagnetic radiation (e.g., light) to facilitate a determination of presence, absence, or amount of one or more particular analytes of interest in a sample. Numerous optical techniques have been developed to employ the evanescent wave from optical waveguides in biosensing applications.

For example, the use of optical waveguides for high-throughput sensing can be achieved using either mass (Silzel et al., 1998) or fluorescence (Stimpson et al., 1995; Watkins et al., 1998; Plowman et al., 1999) sensing techniques. Both of these sensing techniques have been demonstrated as useful in waveguides for conducting immunoassays (Silzel et al., 1998; Wadkins et al., 1998; Plowman et al., 1999) and genetic screenings (Stimpson et al., 1995).

When an optical waveguide is used as a so-called "mass sensor", the presence of a captured analyte may be detected or measured by, first, measuring a baseline absorption or refractive index of a capture molecule on or adjacent a surface of the waveguide prior to exposing the capture molecule to a sample and, second, following exposure of the capture molecule to a sample, determining the difference in absorption or refractive index of the capture molecule and any analyte bound, or hybridized, thereto. With this mechanism, the measured signal changes upon hybridization of capture molecules with analytes in the sample. The signal change is in proportion to the mass that lies within the evanescent field of the waveguide.

Waveguide mass sensing techniques typically rely on surface plasmon resonance (SPR) 5, which has been used extensively in optical biosensing (Liedberg et al., 1987). A surface plasmon can exist at the interface between two media, one of which has a negative dielectric constant (Peyghambarian et al., 1993), such as a metal, and can be resonantly excited using a ruled optical grating or prism to obtain phase matching. The index perturbation of the analyte disturbs this resonance, with greater perturbation provided with larger molecular weight. These sensors have been used for immunoassay (Cullen et al., 1987; Morgan and Taylor, 1992) and molecular diagnostic assay (Watts et al., 1995; Nilsson et al., 1997; Bianchi et al., 1997), and are commercially available (see Malmqvist and Karlsson, 1992, for a review). Affinity sensitivities can be in the nM range (Morgan and Taylor, 1992) for large analyte molecular weight, and 50 µM (Karlsson and Stahlberg, 1995) for small analyte molecular weight, and a sensitivity per unit area of 20 $fM/mm^2$ was measured using resonant mirrors (Watts et al., 1995). Nanoparticles coated with the analyte have also been used to increase mass, leading to a sensitivity of 0.1 pM (Kubitschko et al., 1997). Other waveguide mass sensors are based on light scatter (Stimpson et al., 1995), interferometry (Schneider et al., 1997), and waveguide absorption spectroscopy (Mendes and Saavedra, 1999).

When fluorescence sensing is employed, electromagnetic radiation may be used to create an evanescent wave within an optical waveguide that excites a fluorescent dye, which is also referred to as a fluorophore tag, or a similar tag bound, for example, to a molecule that competes with an analyte of interest for a binding site on a capture molecule immobilized on or adjacent to a surface of the waveguide. The fluorophore tag gives off emitted electromagnetic radiation, the intensity of which is indicative of the presence, absence, or amount of the analyte in the sample.

For optical waveguide sensors that employ fluorescence sensing techniques, the sensitivity depends on affinity strength between each analyte and its corresponding capture molecule, as well as upon the absorption coefficient and fluorescence quantum yield of the fluorophore tag. Fluorescence sensing techniques are generally more sensitive and more specific than mass sensing techniques.

Many of the approaches to fluorescence sensing techniques in optical waveguides are based on the use of optical fiber (Abel et al., 1996; Squillante, 1998), but work has also been performed with planar waveguides (Zhou et al., 1991; Herron et al., 1993; Plowman et al., 1996). Planar waveguide sensors have been used in immunoassay (Zhou et al., 1991; Herron et al., 1993) and molecular diagnostic assay (Plowman et al., 1996) studies, where the latter demonstrated low fM sensitivity.

Nanoparticles have been used as light scattering elements (Yguerabide and Yguerabide, 1991) or as an alternative to fluorophore tags.

When optical waveguides are used, the waveguide may include independent sensing zones on or adjacent to which different types of capture molecules are immobilized. All of the discrete sensing zones of a segmented waveguide can be interrogated in parallel by use of a charge-coupled device ("CCD") array, which can capture the full time dynamics of the affinity interaction. The array size is limited by the patterning of immobilized capture molecules (Silzel et al., 1998) and the sensitivity is limited by the number of captured analytes per sensitivity zone and by the sensing technique employed. Nonetheless, with new patterning techniques, the densities of sensing zones of optical waveguides are continuing to increase (Morgan et al., 1995; Stimpson et al., 1998).

In the state of the art, the sizes of the sensing zones of segmented waveguides are ever-decreasing. Accompanying the decrease in sizes of the sensing zones of segmented waveguides are proportional reductions in the sensitivities with which analytes can be detected by the waveguide. Accordingly, the system requirements of segmented waveguides are becoming ever more stringent.

Moreover, the use of a segmented waveguide is somewhat undesirable since the excitation radiation is not confined within the plane of the waveguide. Consequently, the electromagnetic radiation emitted from one sensing zone may interfere with the electromagnetic radiation emitted from one or more adjacent sensing zones, thereby reducing the optical efficiency of a segmented waveguide and, thus, the degree of confidence with which each analyte may be detected when the segmented waveguide is used. In order to reduce the interference between adjacent sensing zones of segmented waveguides to acceptable levels, the area of each sensing zone to which capture molecules are secured or to which a sample is introduced may be limited to less than 25% of the total area of the sensing zone. As a result, segmented waveguides are relatively insensitive.

A related approach to the optical waveguide is the so-called "biochip", of which the so-called "DNA chip" (Vo-Dinh et al., 1999; Hacia, 1999; Lipshutz et al., 1999) is an example. Biochips, which may be fabricated using self-assembled monolayer or similar patterning techniques, may have very large arrays of sensing zones (e.g., up to 100,000 or more sensing zones). A sample is applied to a biochip, one or more analytes of interest in the sample bind capture molecules on the biochip, and the presence, absence, or amount of each analyte or the hybridization characteristics of the capture substrate with a corresponding analyte is detected in much the same manner as that which is used when segmented waveguides are employed to detect analytes.

For example, fiber optic probes, scanning near-field microscopes, or confocal microscopes may be used to direct one or more wavelengths of electromagnetic radiation into each sensing zone of a biochip to excite fluorescent dyes within the sensing zone. The fiber optic probe or confocal microscope may then be used to detect the electromagnetic radiation emitted from fluorescent labels within each sensing zone. If a fiber optic prove or confocal microscope is used, the biochip may be raster-scanned, one sensing zone at a time. The sensing zones of a biochip can be closely spaced since the probe itself provides lateral optical confinement, which leads to the possibility of biochips with very high sensing zone densities. Such sequential detection is somewhat undesirable, however, because of the time required to scan a biochip with a dense array of sensing zones. Moreover, each hybridization reaction occurring on a biochip is typically analyzed when it reaches an endpoint, which may take hours. Further, different reactions may require different hybridization temperatures. As a result, it may be difficult to simultaneously effect a number of different hybridization reactions on a single biochip, which further increases the amount of time required to obtain results from raster-scanned biochips.

While parallel detection techniques may also be used to simultaneously analyze multiple sensing zones on biochips, parallel detection techniques may also be complicated by the different temperature dependences of different hybridization reactions to be conducted on a single biochip (Fotin et al., 1998). Again, it may be necessary to carry out reactions and to take measurements at a number of temperatures.

In response to these temperature dependence problems, assay techniques have been developed wherein the hybridization rates of different hybridization reactions occurring at different sensing zones of a biochip are simultaneously measured at one or more distinct temperatures or narrow temperature ranges (Jensen et al., 1997).

Another assay technique has been proposed includes effecting different chemical reactions on the surfaces of microspheres (Micheal et al., 1998). The microspheres are deposited into individual wells etched into the distal end of an imaging fiber bundle. Cavity effects of the wells are masked by incoherent illumination, but the use of a CCD to sense reactions on the surfaces of the microspheres may be used in parallel with the imaging fiber bundle.

Flat, or planar, cylindrical microcavities have been used in low-threshold lasers (McCall et al., 1992; Zhang et al., 1995; Baba, 1997) and optical spectral filters (Rafizadeh et al., 1997; Blom et al., 1997; Madsen and Jhao, 1998; Little et al., 1998). These cylindrical microcavities have been fabricated from a variety of materials, including semiconductor materials (e.g., silicon) and glass. Studies have shown that planar cylindrical microcavities with cavity diameters of 10.5 µm may have free spectral ranges (FSRs) of greater than 35 nm and cavity Q values of greater than 8000. Finite-difference time-domain (FDTD) studies (Li and Liu, 1996; Hagness et al., 1997) performed with such planar cylindrical microcavities suggest that FSRs exceeding 100 nm and cavity Q values of $10^4$ or greater are possible with optimized designs. A theoretical study (Little and Chu, 1996) of cavity surface roughness supports these conclusions. Nonetheless, cylindrical microcavities have typically been illuminated from the planar ends thereof, which causes the illuminating electromagnetic radiation to travel throughout the volume of these cylindrical microcavities.

The inventors are not, however, aware of the use of biosensors that include resonant optical cavities that facilitate the use of whispering gallery modes to provide enhanced sensitivity and that have quality factors of at least about $10^4$.

DISCLOSURE OF INVENTION

Whispering gallery modes (WGMs), which are also known in the art as morphology-dependent resonances (MDRs) and as quasi-normal modes (QNMs), occur when light circulates within an optical cavity, reflecting off of a curved boundary of the optical cavity with an angle of incidence that always exceeds the critical angle for total internal reflection. Stated another way, whispering gallery modes occur when electromagnetic radiation (e.g., light) bounces around within an optical cavity. When such movement of electromagnetic radiation within an optical cavity is limited substantially within a single plane, two-dimensional whispering gallery modes are said to occur. If the electromagnetic radiation is reflected within an optical cavity in such a manner that the electromagnetic radiation is not restricted to a single plane, three-dimensional whispering gallery modes are said to occur.

The present invention includes biosensors that include resonant optical cavities that generate and exploit whispering gallery modes, as well as methods of using the biosensors. Biosensors including resonant optical cavities incorporating teachings of the present invention are configured for rapid, high throughput diagnostic assays, as well as in any application where conventional optical biosensors have been employed.

In an exemplary embodiment of biosensor incorporating teachings of the present invention, the resonant optical cavity is a microfabricated structure that includes a flat, or planar, cylinder fabricated upon a substantially planar substrate. The cylinder of the biosensor is referred to herein as a cylindrical optical cavity or simply as a cylindrical cavity. Preferably, the exposed surface of the cylindrical cavity, which is located opposite the substrate, is substantially planar and substantially free of surface defects. A peripheral edge of the cylindrical cavity tangentially abuts at least one electromagnetic radiation transmission port, such as a strip waveguide which, in turn, communicates with a source of electromagnetic radiation, such as a laser.

Capture substrates having a known specificity for one or more particular analytes are immobilized on at least a portion of the exposed surface of the cylindrical cavity. When a sample including the analyte or analytes for which the capture substrates are specific is introduced onto the exposed surface of the cylindrical cavity, at least some of the analyte or analytes in the sample bind to, or hybridize with, capture substrates. Upon illumination of the source, electromagnetic radiation travels through the transmission port into the cylindrical cavity to facilitate sensing of the binding of analyte in the sample to the capture substrate on the exposed surface of the cylindrical cavity.

Another exemplary embodiment of resonant optical cavity according to the present invention includes a bulk cylindrical substrate, such as an optical fiber, with a cylindrical resonant optical cavity formed at an end thereof. As in the microfabricated embodiment, the bulk cylindrical cavity may be tangentially abutted by at least one electromagnetic transmission port, such as a strip waveguide, which, in turn, communicates with a source of electromagnetic radiation. Capture substrates that are disposed on an exposed surface of the cylindrical cavity bind analyte, if present in a sample. Such binding may be detected by introduction of electromagnetic radiation into the cylindrical cavity via the source and transmission port.

The shapes of cylindrical optical cavities incorporating teachings of the present invention facilitate the generation of whispering gallery modes. In the present invention electromagnetic excitation radiation is preferably introduced into a cylindrical cavity through a peripheral edge of the cavity, facilitating the generation of two-dimensional whispering gallery modes within the cylindrical cavity at a substantially planar surface thereof. Whispering gallery modes prolong the exposure of molecules and molecule hybrids on the exposed surface of a cylindrical cavity to electromagnetic excitation radiation.

The cylindrical cavities of the biosensors of the present invention also have very high (e.g., about $10^4$ and greater) quality factors (Q). An optical cavity with a high quality factor typically represents that the intrinsic material absorption of the optical cavity is low, that the contrast between the refractive index of the cavity core and the refractive index of material within the plane of and surrounding the optical cavity is high, and that the cavity diameter, which reduces diffraction losses, is relatively large. The quality factor of an optical cavity is also higher when scattering caused by roughness on the exposed surface of an optical cavity is relatively low and when the coupling strength between the optical cavity and the adjacent transmission port (e.g., a strip waveguide) is relatively high. Moreover, the quality factor of an optical cavity depends upon the particular whispering gallery mode of the cavity.

In addition, cylindrical cavities that are useful in biosensors incorporating teachings of the present invention have sensitivities that are at least about an order of magnitude greater than the sensitivities of state of the art waveguides.

Biosensors including resonant optical cavities of other configurations that generate sufficient WGMs to provide very high quality factors and increased sensitivities over that of state of the art waveguides, such as spherical optical cavities, are also within the scope of the present invention.

Biosensors that incorporate teachings of the present invention are useful in various applications, including, without limitation, clinical diagnostics, environmental and food testing, genomic research, and genetic screening, as well as in other applications where waveguides, biochips, and other assay tools may be employed.

The present invention also includes methods for fabricating resonant optical cavities incorporating teachings of the invention, as well as methods for using biosensors including the resonant optical cavities.

Other features and advantages of the present invention will become apparent to those of ordinary skill in the art through consideration of the ensuing description, the accompanying drawings, and the appended claims.

BRIEF DESCRIPTION OF DRAWINGS

FIG. 3 is a schematic representation of another embodiment of biosensor of the present invention, including a bulk cylindrical resonant optical cavity;

FIG. 3A schematically illustrates a method for fabricating the resonant optical cavity shown in FIG. 3;

FIG. 3B schematically illustrates the inclusion of a plurality of different sensing zones on a surface of the resonant optical cavity shown in FIG. 3;

FIG. 4 is a schematic representation of a spherical resonant optical cavity incorporating teachings of the present invention.

BEST MODE FOR CARRYING OUT THE INVENTION

Design of Resonant Optical Cavities

Figure 1:
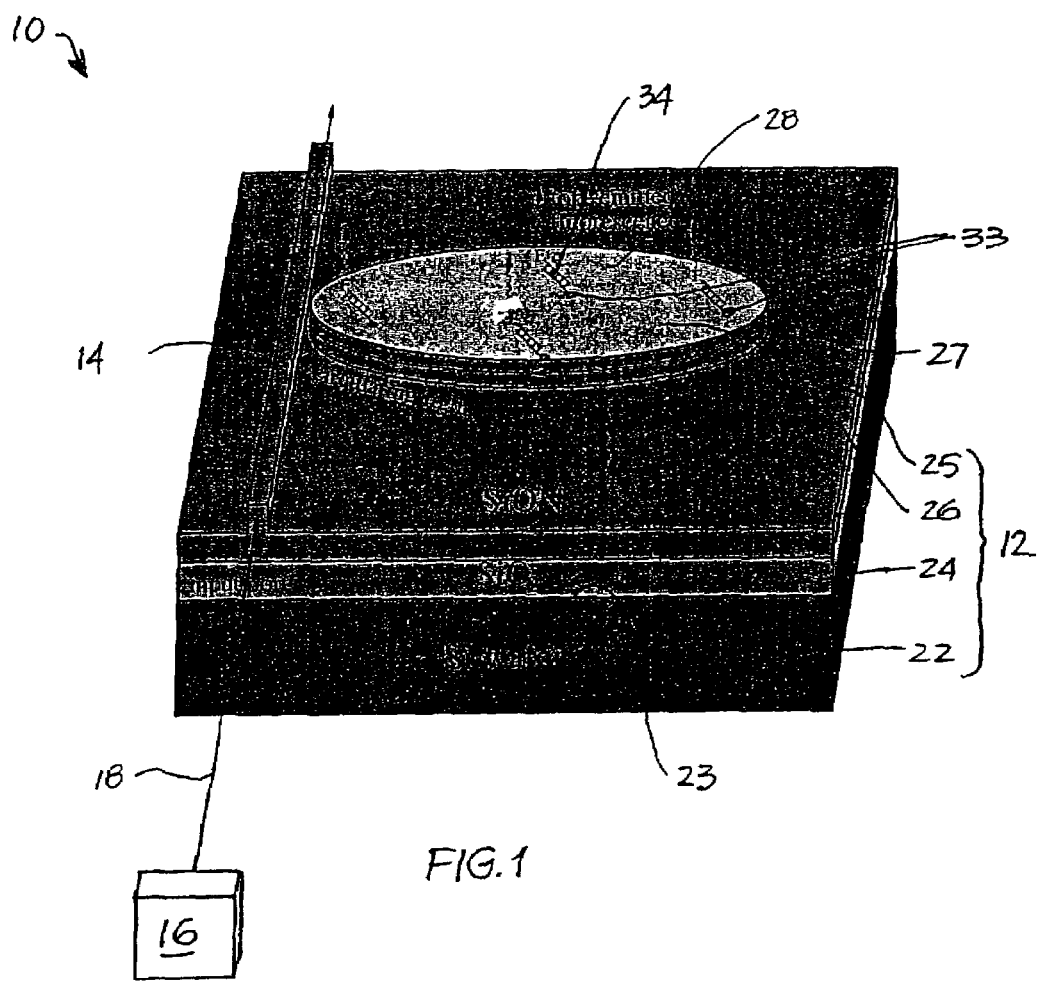
FIG. 1 is a schematic representation of an embodiment of biosensor of the present invention, including a microfabricated cylindrical resonant optical cavity.

Resonant optical cavities incorporating teachings of the present invention are designed to take advantage of two-dimensional whispering gallery modes (WGMs) which possess quality factors (Q) that exceed the quality factors of conventional waveguides. The Q of an optical cavity typically increases with a decrease in the intrinsic absorption of electromagnetic radiation by the material of the optical cavity, an increase in the contrast between the refractive index of the optical cavity and that of the surrounding index that lies in the plane of the optical cavity (which leads to stronger guidance), and an increase in the diameter of the optical cavity (which reduces diffraction losses). The Q of an optical cavity also increases with reduction of surface roughness scattering due to etching of the cavity boundary and reduction of the coupling strength with the adjacent strip waveguide and strongly depends on the particular whispering gallery mode of the optical cavity.

The resonant optical cavities of the present invention are designed to have quality factors of at least about $10^4$ and as high as about $10^9$ or greater. Such high quality factors generally increase the length of time that a photon (i.e., electromagnetic radiation) remains with the optical cavity, which, in turn leads to an increased intensity of electromagnetic radiation within the optical cavity, as well as to increase in the rate at which electromagnetic radiation is spontaneously emitted from the cavity.

In addition, when used in biosensors that employ fluorescence techniques, resonant optical cavities according to the invention may be designed such that high-Q resonance occurs at the peaks of both the wavelengths of electromagnetic excitation radiation that excite, or are absorbed by, fluorescent tags and the fluorescence, or emitted wavelengths, of electromagnetic radiation given off by the fluorescent tags. Resonance at these two peaks is referred to as "double resonance". Accordingly, the increased rate of spontaneous emission of electromagnetic radiation from the resonant optical cavity enhances the yield of fluorescence, while fluorescence emitted from the fluorescent tags may be reabsorbed by the cylindrical cavity, further excite the fluorescent tags, and thereby increase the intensity of fluorescence emitted from the tags. It is believed that, at least when fluorescence sensing techniques are employed, "doubly-resonant" optical cavities are about 10 times (i.e., an order of magnitude) or more sensitive that singly-resonant optical cavities.

The free-spectral range (FSR) of an optical cavity is the frequency separation between adjacent longitudinal modes. Enhancement of fluorescent yield occurs when the free-spectral range of the cavity exceeds the linewidth of electromagnetic radiation emitted from the fluorescent tags. The free-spectral range of an optical cavity is determined by the cavity size and refractive index. Fluorescent yield may be optimized through designing the optical cavity to have a particular free-spectral range and Q and by selecting fluorescent tags with a desirable fluorescence linewidth, which is ideally narrow and matched to the resonance linewidth of electromagnetic excitation radiation within the optical cavity. While solvent (e.g., the aqueous solution of a sample) surrounding the fluorescent tags may cause inhomogeneous broadening of the fluorescence linewidth, solvation dynamics may counteract this effect through dynamic spectral narrowing, through spectral diffusion, of the electromagnetic emitted radiation, which may enhance fluorescence yield and cause the linewidth of the fluorescent, emitted radiation to more closely match the linewidth of the excitation radiation.

For a cylindrical, or disk-shaped cavity, the Q of a particular radial mode, or path of electromagnetic radiation through pattern of motion through the cylindrical cavity, depends upon the closeness of the radial mode to the peripheral edge of the cylindrical cavity, or the radial mode number. Lower numbered, or order, radial nodes are predominantly confined near the peripheral edge of the cylindrical cavity and have higher Qs. The paths of higher order radial modes extend more centrally within the cylindrical cavity and, while these radial modes have lower Qs, they provide for a greater sensing area on a surface of the cylindrical cavity. Various factors affect the radial modes of electromagnetic radiation through a cylindrical cavity, including, but not limited to, the characteristics of the cylindrical cavity, characteristics of a transmission port coupled to the cylindrical cavity, such as the width and effective refractive index of the transmission port, the size of the gap or space between the transmission port and the cylindrical cavity, and the spectral bandwidth of a source of electromagnetic radiation communicating with the cylindrical cavity through the transmission port. Accordingly, the various radial modes of electromagnetic radiation through a cylindrical cavity can be controlled by controlling the characteristics and manner in which an electromagnetic radiation transmission port is associated with the cylindrical cavity, the characteristics of the cylindrical cavity, and the characteristics of the source of electromagnetic radiation.

In designing a cylindrical resonant optical cavity incorporating teachings of the present invention, the sensitivity of the cylindrical cavity may be maximized by determining the optimal distribution of, or balance between, modes with high Qs and modes that cover a large surface area along a planar surface of the cylindrical cavity. Such an optimal distribution may be determined, for example, through analytical results and finite-difference time-domain (FDTD) simulations.

In addition to considering the characteristics of the cylindrical cavity, the transmission port, and the source of electromagnetic radiation, capture substrates immobilized relative to a planar surface of the cylindrical cavity and any adhesion facilitator necessary to immobilize the capture substrate may also have an effect on the initial Q (i.e. Q prior to the binding of analyte by the capture substrate) of the cylindrical cavity. The effects of the capture substrate and adhesion facilitator on the Q of a cylindrical cavity may be caused by the capture substrate and adhesion facilitator having a lower refractive index than that of the cylindrical cavity (e.g., a capture substrate monolayer of neutravidin coupled to a biotin-T3 oligonucleotide has a fixed refractive index of about 1.33, while a silicon oxynitride optical cavity has a refractive index of about 1.5 to about 2.2). The loss of radiation may lower Q and alter the positions of resonances with the optical cavity. Conversely, the loss of radiation from the optical cavity may cause a greater portion of each radial mode with the optical cavity to be involved in the sensing process, effectively increasing the sensitivity of the optical cavity. Accordingly, a cylindrical cavity of the present invention may be designed so as to account for these effects of radiation loss, which may be evaluated by way of known processes, such as numerical simulation with experimental feedback. The loss of radiation may then be appropriately controlled by regulating the thickness of the optical cavity and the refractive indices of the optical cavity and an underlying contrasting layer.

When taking all of the these factors in consideration while designing a resonant optical cavity, Q values of about $10^4$ and greater can be obtained.

Exemplary Biosensor Embodiments

With reference to FIG. 1, an exemplary embodiment of a biosensor 10 incorporating teachings of the present invention is illustrated. As illustrated, biosensor 10 includes a resonant optical assay structure 12, at least one transmission port 14 in communication with resonant optical assay structure 12, and a source 16 of electromagnetic radiation 18 in communication with transmission port 14.

Resonant optical assay structure 12 may include a substrate 22 of glass, quartz, silicon, or another semiconductive material (e.g., gallium arsenide or indium phosphide), a contrasting layer 24 over substrate 22, and a flat, cylindrical resonant optical cavity, which is also referred to herein as a cylindrical cavity 26, positioned over contrasting layer 24. Contrasting layer 24 is preferably formed from a material that has a refractive index that contrasts the refractive index of the material that forms cylindrical cavity 26. Cylindrical cavity 26 may be laterally surrounded by a material layer 25. It is preferred that, for wavelengths of electromagnetic radiation with which cylindrical cavity 26 is to be illuminated, the contrast between the refractive indices of cylindrical cavity 26 and contrasting layer 24 be greater than about 1:1 (i.e., that cylindrical cavity have a refractive index that exceeds the refractive index of contrasting layer 24) and is preferably at least about 1.5:1.

By way of example only, and not to limit the scope of the present invention, when silicon dioxide ($SiO_2$) is used in contrasting layer 24, silica (i.e., doped $SiO_2$, such as borosilicate glass, phosphosilicate glass, or borophosphosilicate glass), silicon oxynitride ($SiO_xN_y$, or SiON), or another suitable material having a higher refractive index than the material of contrasting layer 24 may be used to form cylindrical cavity 26. In addition to having a desirable refractive index, SiON, unlike most popular semiconductor compatible media, has very low loss (0.2 dB/cm or lower, including material and scattering losses) in the visible spectrum of electromagnetic radiation. This gives tremendous flexibility in the choice of optical wavelengths that can be utilized when cylindrical cavity 26 is formed from SiON.

The diameter of cylindrical cavity 26 preferably imparts cylindrical cavity with the desired quality factor. Small cylindrical cavity 26 diameters facilitate the fabrication of large, dense sensor arrays. Exemplary cylindrical cavities 26 incorporating teachings of the present invention have diameters of about 10 µm to about 50 µm, which facilitates the fabrication of sensor arrays having densities of up to about 500×500 cylindrical cavities 26 per square centimeter ($cm^2$).

An exposed major surface 28 of each cylindrical cavity is preferably substantially planar and substantially free of surface defects. Capture substrates 34, including, but not limited to, antibodies, antigens, other polypeptides, nucleotides (RNA or DNA), and cells, that are specific for one or more analytes of interest may be immobilized on or adjacent to surface 28 of each cylindrical cavity 26.

Referring now to FIGS. 1A-1F, conventional semiconductor device fabrication techniques, which are also referred to as microfabrication techniques) may be employed to fabricate resonant optical assay structure 12. By way of example only, substrate 22 may be provided as a full or partial wafer of semiconductive material (e.g., silicon, gallium arsenide, or indium phosphide), or as a silicon-on-insulator (SOI) type substrate (e.g., silicon glass (SOG), silicon on sapphire (SOS), or silicon on ceramic (SOC)).

Figure 1A:
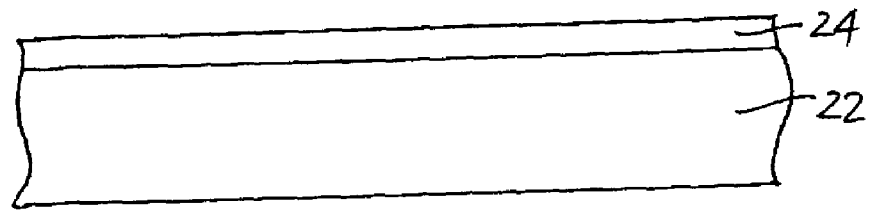
FIGS. 1A-1F schematically depict a method for microfabricating the resonant optical cavity shown in FIG. 1.

As shown in FIG. 1A, contrasting layer 24 of a desired material may be formed on substrate 22 by known processes. For example, in embodiments of the invention wherein $SiO_2$ is employed as contrasting layer 24, $SiO_2$ of a desired depth may be formed on an active surface 23 of substrate 22 by use of known oxidation processes (e.g., thermally, by exposing active surface 23 to oxidants, etc.). Alternatively, the $SiO_2$ of contrasting layer 24 may be deposited onto active surface 23 by known processes, such as by chemical vapor deposition (CVD).

Figure 1B:
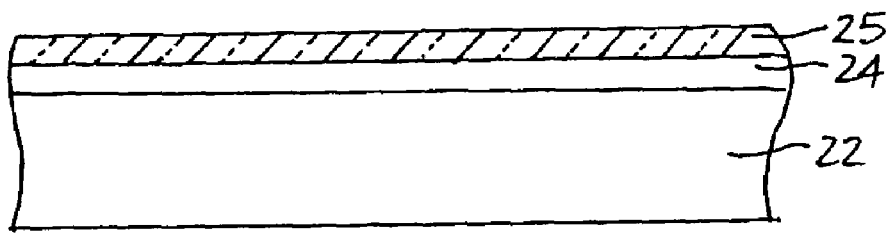

Turning to FIG. 1B, a material layer 25 from which cylindrical cavity 26 will subsequently be formed may be disposed over contrasting layer 24 by known processes. As an example, a layer 25 of silica, or glass, may be formed over contrasting layer 24 by known processes, such as by use of known CVD or spin-on glass (SOG) techniques. Alternatively, a layer 25 of SiON may be fabricated, for example, by known CVD processes.

Figure 1C:
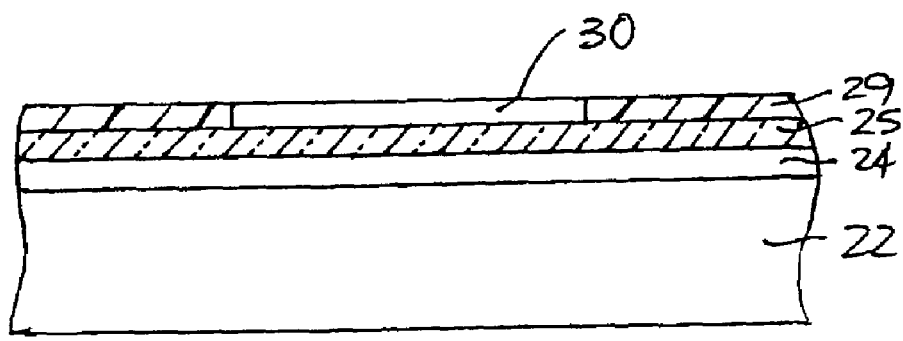

Layer 25 may also be patterned by known processes. By way of example, as depicted in FIG. 1C, a photomask 29 covering the regions of the underlying layer 25 to be patterned, which is known as either a positive or a negative photomask, may be formed by disposing a photoresist by way of known photolithography processes, including, without limitation, the use of a reticle or photomask having high resolution (e.g., about 0.5 µm or smaller), or e-beam lithography, which may be used to facilitate the formation of cylindrical cavities 26 of small dimensions (e.g., about 10 µm to about 50 µm in diameter) with high resolution (i.e., minimized radiation scattering).

Figure 1D:
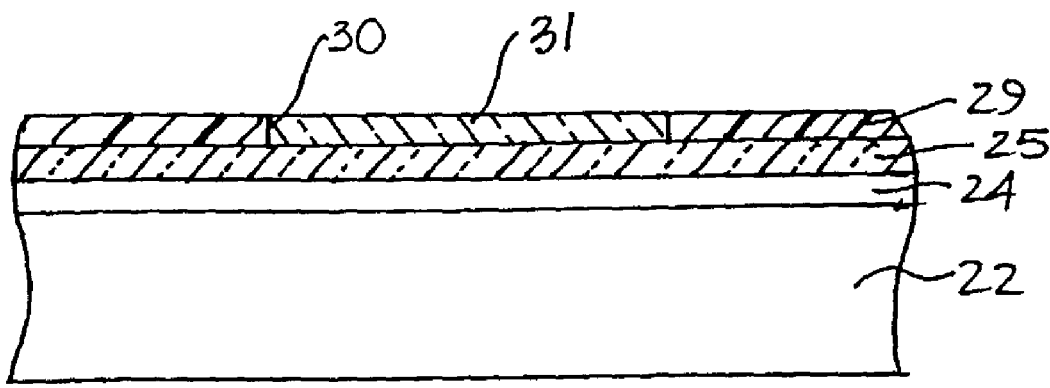
Figure 1E:
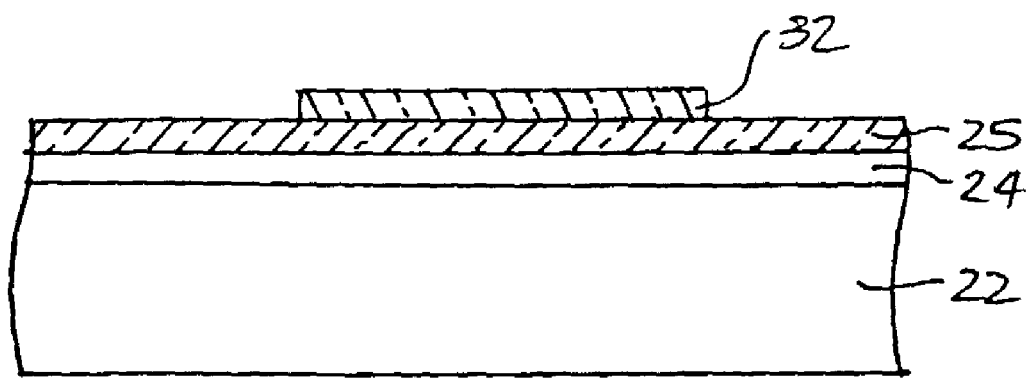

As shown in FIG. 1D, apertures 30 through photomask 29 may be filled with another mask material 31, such as a metal or $SiO_2$, that will withstand the process that will be used to etch layer 25. Mask material 30 is removed from locations overlying photomask 29 by known techniques, such as wet dip processes or mechanical or chemical-mechanical polishing processes, to form a hard mask 32, as shown in FIG. 1E. Photomask 29 is then removed from layer 25, also by known processes, such as by use of resist strippers.

Figure 1F:
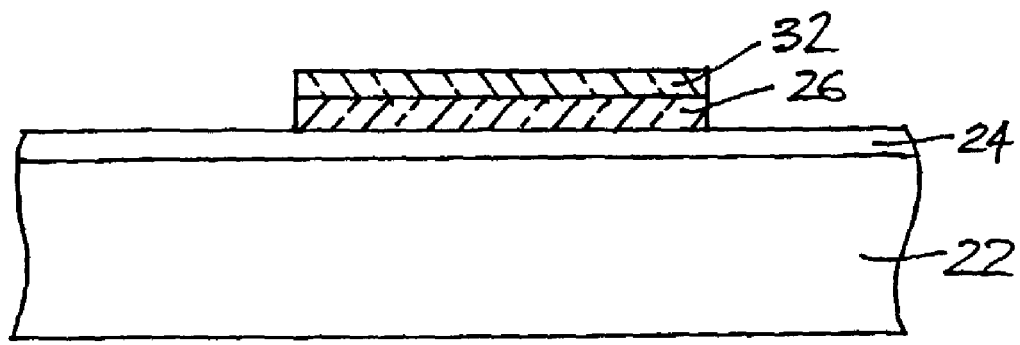

Referring to FIG. 1F, as it is preferred that the peripheral edges 27 of cylindrical cavities 26 be oriented substantially perpendicularly relative to the plane of substrate 22, known anisotropic etching techniques, such as reactive ion etching (RIE), may be used to remove the material of layer 25 through hard mask 32 to form cylindrical cavities 26 from the material of layer 25.

The material of hard mask 32 may then be removed from above cylindrical cavities 26 by known processes, such as by use of etching processes that are selective over the material from which cylindrical cavities 26 are formed.

Transmission port 14 may be fabricated on substrate 22 in the same manner as its corresponding cylindrical cavity 26, either simultaneously with the fabrication of cylindrical cavity 26 or separately therefrom.

Alternatively, a separately fabricated transmission port 14, such as a known strip waveguide or optical fiber, may be assembled with resonant optical assay structure 12 so as to abut a peripheral edge 27 of at least one cylindrical cavity 26 formed on substrate 22. In any event, transmission port 14 may be coupled to or otherwise communicate with source 16 as known in the art.

Figure 2A:
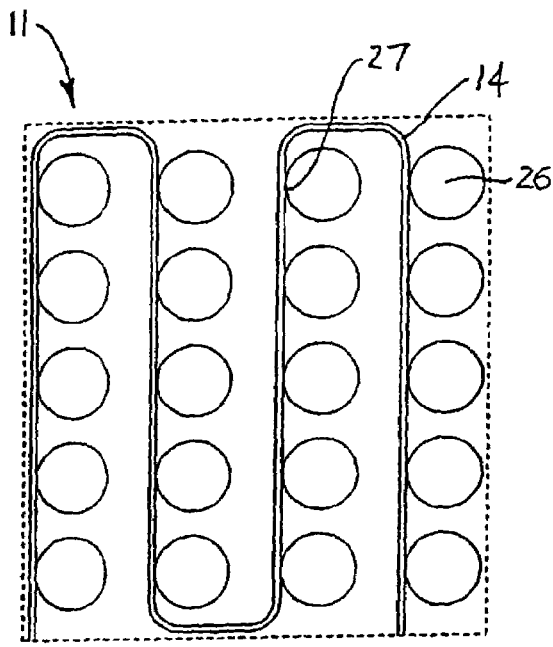
FIGS. 2A and 2B are schematic representations illustrating exemplary manners in which transmission ports may supply electromagnetic radiation to each of the resonant optical cavities of FIG. 1 included in an array of resonant optical cavities.
Figure 2B:
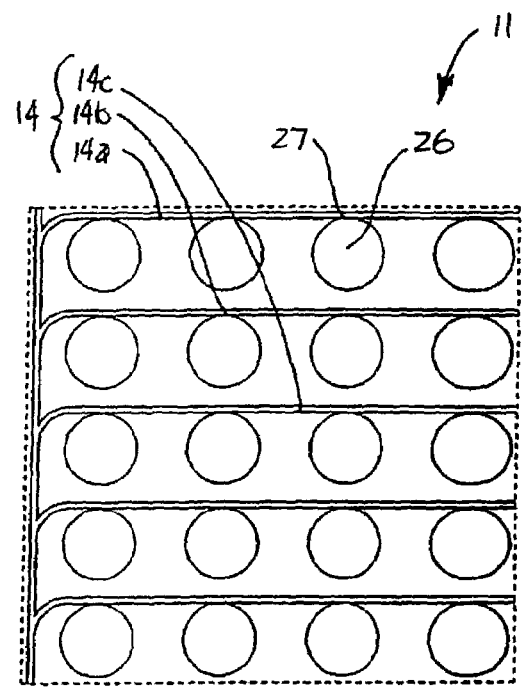

As shown in FIGS. 2A and 2B, examples of the manner in which a transmission port 14 may feed excitation electromagnetic radiation to an array 11 of microfabricated cylindrical cavities 26 are illustrated. For example, transmission port 14 may comprise an optical distribution network that feeds each cylindrical cavity 26 of array 11. As depicted in FIG. 2A, transmission port 14 includes a single optical bus that feeds each cylindrical cavity 26 in series, making 180° turns at the end of each column of array 11 of cylindrical cavities 26.

Alternatively, as shown in FIG. 2B, transmission port 14' may include a separate waveguide 14a, 14b, 14c, etc., to feed electromagnetic excitation radiation into cylindrical cavities 26 of each column or row of array 11. Transmission port 14' is also referred to as a "tree-bus network".

As a finite amount of excitation radiation is lost from each cylindrical cavity 26, the intensity of electromagnetic excitation radiation remaining within transmission port 14, 14' drops in series after the radiation is fed to each cylindrical cavity 26. Accordingly, the cavity coupling fraction between transmission port 14, 14' and each cylindrical cavity 26 preferably increases in series so as to facilitate the feeding by transmission port 14, 14' of a substantially uniform intensity of electromagnetic excitation radiation to each cylindrical cavity 26 along the length of each transmission port 14, 14'.

Referring again to FIG. 1, an adhesion facilitator 33 may be applied to a surface 28 of each cylindrical cavity 26 to facilitate the immobilization of one or more capture substrates 34 to surface 28. By way of example, and not to limit the scope of the present invention, neutravidin may be absorbed to surface 28 to facilitate the immobilization of biotinylated nucleic acids (e.g., RNA or DNA, including oligonucleotides) adjacent to surface 28.

Capture substrates 34, including, without limitation, proteins (e.g., antibodies and antigens), peptides, nucleic acids (e.g., DNA and RNA), other biomolecules, and microorganisms such as bacteria and viruses, may be disposed and immobilized on or adjacent to surface 28 of each cylindrical cavity 26 by known processes. For example, a solution including an appropriate concentration of capture substrates 34 may be placed onto surface 28 or onto a adhesion facilitator 33 on surface 28, a process which is typically referred to in the art as "puddle coating". Surface 28, any adhesion facilitator 33 thereon, and capture substrates 34 may then be exposed to an appropriate temperature for an appropriate amount of time to immobilize capture substrate 34 relative to surface 28 (i.e., a temperature and duration that will facilitate adsorption of capture substrates 34 to surface 28 or to a adhesion facilitator 33 on surface 28 without degrading capture substrates 34 or adversely affecting the ability of capture substrates 34 to bind to, or hybridize with, an analyte of interest).

As an alternative to the disclosed use of avidin-biotin chemistries to immobilize biomolecules relative to surface 28, known epoxysilane chemistries may be useful for immobilizing capture substrates 34, such as nucleotides (i.e., DNA and RNA) and other biomolecules, to surface 28.

As an example of a method that may be used to secure capture substrates 34 to surface 28, an atomic layer of gold may be applied to surface 28, a biotinylated thiol adsorbed to the gold, and hydrophobic silane applied laterally around cylindrical cavity 26, or between adjacent cylindrical cavities 26 of an array. The biotinylated thiol, which is hydrophilic, facilitates the immobilization of capture substrates 34 relative to surface 28, while the hydrophobic silane prevents capture molecules from absorbing to features that are laterally adjacent to surface 28, as well as preventing lateral cross-contamination of different types of capture molecules 34, such as those secured to adjacent cylindrical cavities 26.

Other heterologous immobilization techniques (i.e., techniques that facilitate the application of different types of capture molecules 34 to dense arrays of optical cavities) include, but are not limited to, self-assembly processes, photopatterning, and combinatorial synthesis.

Referring now to FIG. 3, another exemplary embodiment of biosensor 10' incorporating teachings of the present invention is depicted. Biosensor 10' includes a resonant optical cavity 12' in the form of a bulk cylindrical cavity 26' formed on an end of a bulk cylindrical substrate 22'. At least one transmission port 14 abuts or is disposed adjacent a peripheral edge 27' of bulk cylindrical cavity 26' so as to communicate with optical cavity 12'. Transmission port 14 also communicates with a source 16 of electromagnetic radiation 18.

As an example of the fabrication of bulk cylindrical cavity 26', FIG. 3A illustrates that a rod 25' formed from a suitable material may be diced into several thin disk-shaped segments 25a', 25b', 25c', etc., each of which will eventually comprise a bulk cylindrical cavity 26'. Rod 25' may be either a solid fiber or a hollow, capillary fiber. While rod 25' is preferably formed from glass, any other suitable waveguide material may be used. While rod 25' may have any diameter, it is preferred that rod 25' have a diameter of about 1 mm to about 10 mm and, more preferably, of about 5 mm. Each segment 25a', 25b', 25c', etc. preferably has a height of about 2 mm, although different segment 25a', 25b', 25c', etc. heights are also within the scope of the present invention.

A flat surface 28', or end, of each of disk-shaped segments 25a', 25b', 25c', etc., is polished by known techniques. This polished, flat surface 28' is then diffused, or doped, with a suitable material, such as potassium ions ($K^+$), sodium ions ($Na^+$), or a combination thereof, using known an ion-exchange waveguide fabrication techniques, to form bulk cylindrical cavity 26' at surface 28'. Surface 28' is preferably diffused with such a material to a depth of a few microns.

As shown in FIG. 3B, capture molecules 34 may be immobilized relative to surface 28' in the same manner as that disclosed with respect to the microfabricated embodiment of cylindrical cavity 26 discussed previously herein with reference to FIG. 1. As surface 28' may have a much larger area that surface 28 of cylindrical cavity 26, different types of capture molecules 34 (i.e., different analyzing chemistries) may be immobilized relative to different reaction regions 28a', 28b', 28c', etc. of surface 28'.

Both biosensor 10 and biosensor 10' may include a sensor 40 associated with each cylindrical cavity 26, 26' thereof. As depicted in FIG. 3, sensor 40 includes a CCD array operatively associated with a processor 50 (e.g., a PENTIUM-class microprocessor manufactured by Intel Corporation of Santa Clara, Calif.). In biosensor 10 (FIG. 1), each cylindrical cavity 26 of an array is aligned with at least one corresponding pixel 42 of the CCD array of sensor 40. A conventional CCD array may be used to screen as many as about $10^5$ or more cylindrical cavities 26 of an array. In biosensor 10' (FIG. 3), each reaction region 28a', 28b', 28c', etc. of surface 28 is aligned with at least one corresponding pixel 42. As electromagnetic radiation is emitted from surface 28 of a specific cylindrical cavity 26 of biosensor 10 or from a specific reaction region 28a', 28b', 28c', etc. on surface 28' of biosensor 10', processor 50 collects data from the one or more corresponding pixels 42 of sensor 40 and, based upon stored information regarding the type of capture substrate 34 immobilized relative to the corresponding surface 28 or reaction region 28a', 28b', 28c', etc., generates and outputs data regarding the presence of one or more analytes in a sample, the quantity of analyte in the sample, or the hybridization kinetics between capture substract 34 and a corresponding analyte in the sample. Of course, other known types of sensors may also be employed with biosensors 10, 10' to detect electromagnet radiation emitted from cylindrical cavities 26, 26'.

With reference to FIG. 4, a biosensor 10" including another embodiment of resonant optical cavity 26" incorporating teachings of the present invention is illustrated. Resonant optical cavity 26" is spherical in shape and includes a suitable substrate (e.g., doped or undoped $SiO_2$, SiON, etc.), the surface 28" of which is diffused, or doped, with a suitable material, such as potassium ions ($K^+$), sodium ions ($Na^+$), or a combination thereof, using known an ion-exchange waveguide fabrication techniques. Resonant optical cavity 26" may be substantially completely doped, or only the portions of cavity 26" proximate surface 28" may be doped. A capture substrate 34 may be applied to surface 28" as described previously herein.

Resonant optical cavities 26" may be held within a carrier of desired shape and associated with at least one transmission port 14, source 16, and sensor 40 (See, e.g., FIG. 3).

Any of the embodiments of resonant optical cavities disclosed herein may be reused by stripping capture substrate 34 from surfaces 28, 28', 28", then applying capture substrate of the same or a different type to surfaces 28, 28', 28".

Sensing Methodologies

Mass Sensing

Due to the high Qs of resonant optical cavities incorporating teachings of the present invention, the resonances of these optical cavities are sensitive to small refractive or absorptive perturbations that are caused by the hybridization of analytes with the immobilized capture substrates. Due to the sensitivities of the optical cavities to these perturbations, biosensors incorporating teachings of the present invention may employ mass sensing techniques, such as in surface-plasmon resonance (SPR) techniques, to determine whether one or more analytes are present in a sample, to quantify the one or more analytes in a sample, or to evaluate the hybridization kinetics between a capture substrate and a corresponding analyte.

The average refractive index of capture substrate and any adhesion facilitator on a surface of a resonant optical cavity according to the present invention is increased as analyte binds, or hybridizes with, the capture substrate. This increase in the refractive index of an optical cavity causes a shift in the resonance of the optical cavity, lowering the Q of the optical cavity at the wavelength of electromagnetic radiation used to detect the presence of analyte, an effect which is referred to as "Q-spoiling". Known processes, such as spectroscopic or intensity measurements of electromagnetic radiation attenuated by the capture substrate and any analyte hybridized therewith, may be used to detect such a shift of the resonance of the optical cavity. The sensitivity with which such measurements may be made is directly proportionate to the Q of the optical cavity. Mass sensing is particularly useful in applications where it is not desirable to label an analyte or a molecule that competes with the analyte for a binding site on the capture substrate.

Figure 5:
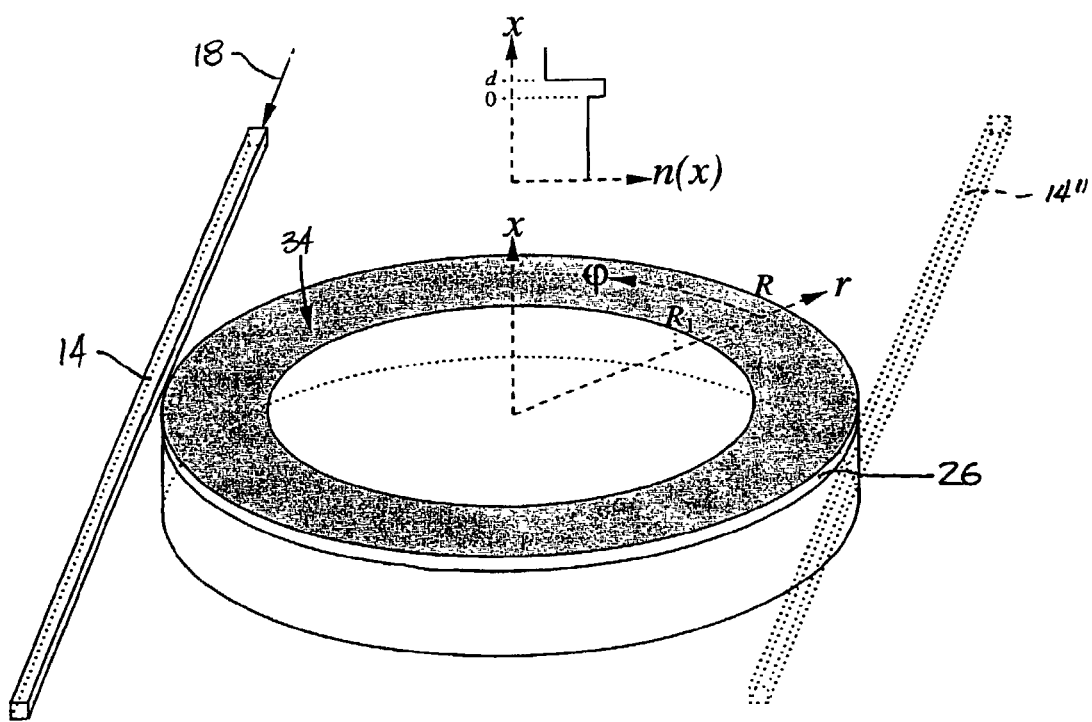
FIG. 5 depicts the use of a reflection port with the biosensor shown in FIG. 1 to facilitate the use of mass sensing techniques.

An alternative and more practical method to detect the presence of the analyte bound to the capture substrate is to position a reflection port 14" (e.g., a strip waveguide) adjacent to a surface of the optical cavity (e.g., cylindrical cavity 26), as shown in phantom in FIG. 5. This reflection port 14" couples light out of cylindrical cavity 26. As the resonance of cylindrical cavity 26 shifts, the intensity of electromagnetic radiation exiting cylindrical cavity 26 through reflection port 14" decreases. The change in the ratio of the intensity of electromagnetic radiation exiting cylindrical cavity 26 through reflection port 14" to the intensity of electromagnetic radiation introduced into cylindrical cavity 26 by transmission port 14 may be related to the affinity concentration of the analyte bound by capture substrate 34.

Since mass sensing techniques require only one wavelength of electromagnetic radiation to detect or quantify an analyte, when mass sensing techniques are employed, biosensors of the present invention need only include resonant optical cavities that resonate at that one wavelength of electromagnetic radiation.

Fluorescence Sensing

Fluorescence sensing techniques may also be used with biosensors of the present invention to determine the presence of an analyte in a sample, the amount of analyte in a sample, or the hybridization kinetics between a capture substrate and a corresponding analyte in a sample. When fluorescence sensing techniques are used, an analyte molecule or a molecule that competes with the analyte for binding sites on the capture substrate is labeled with a fluorescent tag, which preferably emits electromagnetic radiation of a different wavelength than that which excites the fluorescent tag. Accordingly, the wavelength of electromagnetic excitation radiation should lie within the absorption band, or range of absorbable wavelengths, of the fluorescent tag. For example, the optimal wavelength of electromagnetic radiation for exciting fluorescent tags may lies somewhere in the blue-green to green portion of the spectrum.

When used in biosensors incorporated teachings of the present invention, the resonant optical cavities of these biosensors prolong the lifetimes of photons of the electromagnetic excitation radiation. These long photon lifetime result in an effective sensing length that is much longer than the actual distance across the surface of the cavity, but within a surface area that is considerably smaller than that of a conventional slab waveguide sensor, for which femtomolar (fM) ($10^{-15}$ M) sensitivity has been achieved. In addition, the high intensity of excitation radiation within a resonant optical cavity of the present invention may induce fluorescent tags to absorb multiple photons of excitation radiation, which may provide the further advantages of substantially background-free and high sensitivity detection of analytes.

As at least two wavelengths of electromagnetic radiation are used to detect or quantify an analyte when fluorescence sensing techniques are employed (one excitation, one emission), it is preferred that fluorescence sensing techniques be used with resonant optical cavities according to the present invention that resonate at the wavelength peaks of both the excitation radiation and the radiation emitted from the chosen fluorescent tags.

Two-Photo Absorption Sensing

The large buildup of excitation radiation within a resonant optical cavity results in high intracavity intensity of the excitation radiation, which can induce fluorescent tags to emit when two-photons are absorbed. The wavelength of fluorescent, emitted radiation is significantly smaller than the wavelength of absorbed, excitation radiation such that any one-photon scatter from the excitation source, such as surface scatter, Raleigh scatter, inelastic scatter, or any source of one-photon fluorescence, can be completely removed by a high-pass optical filter. For a washless assay, two-photon fluorescence from unbound oligonucleotides is a negligible source of interference. Different fluorescent tags are studied to obtain the highest two-photon cross-section for maximum sensitivity.

In order to efficiently induce fluorescence via two-photon absorption, the wavelength of the source of electromagnetic radiation should be longer than the wavelength peak for one-photon absorption by the fluorescent tag, but shorter than two times the wavelength peak for one-photon absorption. This condition places some constraints on the source and the fluorescent tag. Due to the commercial availability of 980 nm laser diodes with single-mode powers up to about 200 mW, candidate fluorescent tags include fluorescein, which has an absorption peak of 490 nm, and R6G, which has an absorption peak of 530 nm, among many others. The two-photon cross-section of these fluorescent tags is studied in order to maximize interaction with the evanescent wave of the resonant optical cavity.

Due to the difference in the wavelength of excitation radiation that are used to excite fluorescent tags when two-photon absorption sensing is employed and that used in fluorescence sensing techniques to excite fluorescent tags, the resonant optical cavity for a two-photon sensing technique is designed such that resonance is obtained at the appropriate wavelength of excitation radiation. Two-photon fluorescence scales as the square of the intensity of excitation radiation, which varies due to the change in position of the fluorescent tag with respect to the evanescent field.

Two-photon absorption provides more surface selectivity and noise immunity (i.e., signal to background ratio) than one-photon techniques. The sensitivity and specificity of the two-photon technique are believed to be the highest of the three microcavity mechanisms studied.

Uses of Biosensors Including Resonant Optical Cavities

Biosensors incorporating teachings of the present invention and the resonant optical cavities thereof may be used in any application that employs a biomolecular affinity interaction. Thus, the biosensors of the invention are useful in a variety of practical applications, including, without limitation, in clinical diagnostics, environmental testing, food testing, genetic screening, and nucleic acid or protein sequencing. Biosensors according to the present invention may, for example, be embodied as immunoassays (IA) or as nucleic acid hybridization assays, which are also referred to as molecular diagnostic assays (MDx).

As resonant optical cavities incorporating teachings of the present invention may be fabricated in arrays that are comparable to the array sizes of current biochip technology, but with much higher sensitivity than that currently available with current biochip technology and the capability for parallel detection of hybridization kinetics, resonant optical cavity arrays of the present invention may also be used in place of biochips.

Sensitivity of Biosensors Including the Resonant Optical Cavities

Comparison of the Sensitivities of Slab Waveguides and Arrays of Cylindrical Cavities A rough example calculation illustrates the enhanced sensitivity per area of biosensors including cylindrical resonant optical cavities of the present invention over that of biosensors that include conventional slab waveguides. The estimates used in the rough example calculation assume that the optical cavity has a Q of about $10^4$ at a wavelength of 635 nm. The lifetime of a photon within such an optical cavity is about 3.4 picoseconds (ps) ($3.4 \times 10^{-12}$ s), which leads to an effective interaction length between the photon and fluorescent tags on molecules immobilized by the capture substrate to a surface of the resonant optical cavity of about 500 μm, or an effective sensing area of about 500 ($d_c/2$) μm$^2$, where $d_c$ is the cavity diameter, in μm, which may be smaller than 10 μm.

If L is the width of an array of these cylindrical resonant optical cavities, then the number of cavities, or zones, within the device is $L^2/(2d_c)^2$, where the cavity center-to-center spacing is $2d_c$ is small due to the strong lateral confinement provided by the cavities and strip waveguides.

The sensing area per zone for a slab waveguide is approximately $fd^2$ μm$^2$, where f, the sensing zone fill fraction, is equal to 0.25, d is the diameter of the sensing zone, and the number of zones is given by $L^2/(2d)^2$.

Thus, for the same sensitivity per zone, an array of cylindrical resonant optical cavities of the present invention has a density advantage by a factor of about $1000/d_c$ over a conventional slab waveguide and, for the same array size, the microcavities have a sensitivity advantage of $1000/d_c$ over the conventional slab waveguide.

These simple scaling arguments suggest the utility of an array of cylindrical resonant optical cavities incorporating teachings of the present invention in clinical applications that utilize samples with low analyte concentrations and require high throughput. Although these scaling arguments do not take into account a number of engineering factors or the enhanced sensitivity that may result from two-photon fluorescence or the use of doubly-resonant cavities, a dramatic advantage of using microcavity sensor arrays is evident, which may be beneficial in many diverse biosensing scenarios.

As bulk cylindrical cavities incorporating teachings of the present invention can be patterned with multiple monolayers, or analyzing chemistries, bulk cylindrical cavities are believed to have the same desirable properties as microfabricated arrays of cylindrical cavities. In fact, it is expected that bulk cylindrical cavities of the type described previously herein may be designed and fabricated so as to have Qs on the order of about $10^6$ to $10^7$.

It is also expected that small glass spheres with an ion-exchange waveguide surface may be designed and fabricated in accordance with teachings of the present invention so as to have Qs on the order of about $10^7$ or greater.

Increased Sensitivity of Resonant Optical Cavities through Enhanced Quantum Efficiency Relative to Slab Waveguides Another example calculation illustrates the enhanced sensitivity of cylindrical resonant optical cavities of the present invention through enhanced quantum efficiency. Using the notation of B. E. Little, S T. Chu, H. A. Haus, and J.-P. Lame, "Microring resonator channel dropping filters", Journal of Lightwave Technology, 15, 998-1OOS (1997) (hereinafter "Little"), the disclosure of which is hereby incorporated in its entirety by this reference, the overall cavity decay rate can be written $1/\tau = +1/\tau_e + 1/\tau_d + 1/\tau_l$, where $1/\tau_e$ represents the rate at which electromagnetic radiation, or power, is resonantly coupled from the transmission port to the optical cavity, $1/\tau_d$ is the rate at which power is coupled from the optical cavity to the reflection port, and $1/\tau_l$ is the loss rate due to absorption and scattering within the optical cavity. Note that these rates are different for each resonant mode. The total power through the cross-section of the optical cavity and through the transmission port are given by Little:

$$P_{cavity} = \frac{v_g \tau^2}{\pi R \tau_c} P_{inc} \qquad (1)$$

$$P_{trans} = (1 - 2\tau/\tau_c)^1 P_{inc}$$

where $v_g \approx c/n$ is the modal group velocity, R is the radius of the cylindrical cavity, and $P_{inc}$ is the incident power in the cylindrical cavity. The transmitted power is zero, meaning that all incident power couples into the optical cavity, when $1/\tau_c = 1/\tau_d + 1/\tau_l$. Making the assumptions that $1/\tau = 2/\tau_e$, the optical cavity power flow can be written in terms of the Q of the optical cavity:

$$P_{cavity} = \frac{\lambda Q}{2\pi R} P_{inc}, \qquad (2)$$

where λ is the material wavelength. This equation shows the potential for strong optical cavity enhancement given by the factor $\lambda Q/2\pi R$.

The main property used here is that fact that all incident light can be coupled into a traveling-wave resonator, which dramatically enhances quantum efficiency. Internal power is maximized in a two-port device for which $\tau_d \to \infty$ and $\tau_e \approx \tau_l$.

For a fluorescence biosensor, $\tau_l$ consists of contributions from diffraction, scattering, and absorption losses within the optical cavity, absorption, and scattering from the bioselective capture substrate, and absorption by the fluorescent tag. If $\tau_l$ is the cavity lifetime in the absence of the analyte and $\tau_l'$ is the lifetime at a given analyte affinity concentration, which is different than $\tau_l$ due to absorption by the fluorophore, then $Q \propto \tau_l$ and $Q' \propto \tau_l'$. The Q of the optical cavity in the presence of the analyte can be written $1/Q'=1/Q+1/Q_{abs}$, where $Q_{abs}=1/\lambda\alpha$ is the cavity Q due only to absorption by the fluorescent tag, with absorption coefficient $\alpha$. The intensity of the emitted, fluorescent radiation is proportional to the quantum efficiency, which is defined as the fraction of absorbed power into the fluorescent tag, and can be written:

$$\eta_{cav} = \frac{Q'}{Q_{abs}} = \frac{1}{1+Q_{abs}/Q} = \frac{Q}{Q_{abs}} \quad (3)$$

for the resonant cavity. This is a new result. The middle expression clearly illustrates enhanced quantum efficiency when an optical cavity with a high Q is used.

By way of contrast, for a slab waveguide sensor length L, the quantum efficiency $$+72 = 1 - e^{-+60L} \approx +60L \quad (4)$$
$$\overline{wg}$$
$$n_{wg} = 1 - e^{\alpha L} = \alpha L$$

In both cases, the approximations are valid for small $\alpha$, which is always the case in low concentration detection, and it is assumed that the vertically-confined modal profiles of the cylindrical resonant optical cavity and the slab waveguide are the same, such that the effective absorption coefficients are the same due to the overlap of the evanescent field with the absorption region.

The quantum efficiency enhancement factor is $Q/\alpha L Q_{abs} = \lambda Q/L$, such that the quantum efficiencies are equal when the waveguide sensor has length $L=Q\lambda$, which is exactly the effective length of the resonant optical cavity. For a slab waveguide region of length $L=2\pi R$ (equal to the cavity circumference), a cylindrical resonant optical cavity of the same circumference has a quantum efficiency that is enhanced by a factor of $\lambda Q/2\pi R$, which is the same as predicted by equation (2). Thus, in order to have the same quantum efficiency as a cylindrical resonant optical cavity of the present invention, a conventional slab waveguide must be relatively long.

Benefits of the Increased Sensitivities of Resonant Optical Sensors

The advantage of using a resonant optical cavity incorporating teachings of the present invention can be best exploited in two sensing scenarios: 1) highly sensitive detection of a single or small number of analytes using bulk cavities and 2) high-throughput sensing of a large number of analytes using microcavity arrays.

In the first case, a mode of a bulk cylindrical cavity with diameter of about 1 mm to about 10 mm may have a Q of about $10^6$, with a quantum efficiency equal to that of a conventional slab waveguide sensor of length L=0.5 m (assuming a material wavelength $\lambda=0.5$ µm), which is an impractical size for a slab waveguide. Thus, a bulk cylindrical cavity having about the same area as a slab waveguide will have a quantum efficiency of about 100 times that of the slab waveguide, which leads to a sensitivity advantage by a factor of about 10 (i.e., about one order of magnitude). As a result, smaller sample sizes having lower analyte concentrations may be assayed with resonant optical cavities incorporating teachings of the present invention.

Similar arguments hold for the smaller, microfabricated cylindrical cavities, which may have diameters of about 50 µm or less. Assuming that a microfabricated cylindrical cavity has a Q of about $10^4$, the equivalent length of a slab waveguide would be about 5 mm, which is a practical size. Nonetheless, due to its small size, the microfabricated cylindrical cavity may be included in a dense array of cylindrical cavities. Accordingly, a number of hybridization reactions may be effected simultaneously and detected with at least the same sensitivity of a much larger slab waveguide.

The present invention is further detailed in the following EXAMPLES, which are offered by way of illustration and are not intended to limit the invention in any manner. Standard techniques well known in the art or the techniques specifically described below are utilized.

EXAMPLE 1

Development of Optical Microcavities

In determining the mass sensitivity of resonant optical cavities incorporating teachings of the present invention, calibration curves indicating the sensitivity per unit area of these resonant optical cavities may be generated and compared with the sensitivities of known mass sensing apparatus, such as the BIAcore surface-plasmon resonance apparatus.

Studies are initially performed using large diameter (about 25-50 µm) cylindrical cavities. There are many design parameters that affect the cavity FSR, Q, and mode structure. This parameter space is explored initially using FDTD simulation.

When optimized design parameters are obtained, the cylindrical cavities are fabricated. Using a laser diode with tunability over the absorption band of the target fluorescent tag and a high-sensitivity photoreceiver, the cavity free-spectral range (FSR) and Q of the cylindrical cavities are measured and compared with the results obtained through FDTD simulation.

Smaller cylindrical cavities may then be microfabricated. Again, feedback from characterization and simulation guide further lithography and fabrication steps to obtain cylindrical resonant optical cavities with the desired, high Q.

EXAMPLE 2

Nucleic Acid Probe Assay

After proper device characterization, nucleic acid assay studies are performed. Nucleic acid probes are chosen because they stand to benefit the most from the high throughput capability of the microfabricated array embodiment of biosensor disclosed previously herein. The T3 RNA polymerase promotor site is the model system for nucleic acid hybridization. These synthetics mimic single-stranded oligonucleotides amplified from human DNA using polymerase chain reaction (PCR) and, while T3 has minimal clinical relevance, the T3 hybridization process has been well characterized and serves as an ideal baseline for initial studies, which can be readily extrapolated to assays with clinical relevance.

Capture oligonucleotides (T3 for the baseline studies) are immobilized relative to the substantially planar surface of a SiON cylindrical cavity by coating the substantially planar surface with neutravidin using a simple puddle coating technique and immobilizing biotinylated T3 to the neutravidin-coated surface. The capture oligonucleotides are exposed to a solution including a known concentration of the complementary oligonucleotides, referred to as "anti-T3", which hybridize with the capture oligonucleotides. Oligonucleotide primers for the T3 sequence and the complementary anti-T3 sequence are commercially available, and have been fluorescently labeled.

The hybridization kinetics are interrogated using the mass, fluorescence, or two-photon absorption sensing techniques described previously herein. The hybridization kinetics of binding between T3 and anti-T3 is probed by the evanescent field of the cylindrical cavity mode, where the excitation radiation is strobed for about 10 to about 15 seconds for detection at periodic time intervals of about 1 minute over the course of about 5 minutes. The rate of hybridization, to within a constant that depends on the properties of the biosensor, is determined based on measurements taken with each illumination of the cylindrical cavity. The constant, referred to as a "sensor gain factor", has a much larger value for a biosensor including a microfabricated cylindrical cavity than for a conventional slab waveguide and produces the increase in analytical sensitivity of the resonant optical cavity of the present invention.

These measurements are repeated for a logarithmic progression of anti-T3 concentrations so that the analytic sensitivity can be calculated from the standard curve. Each of the mass, fluorescence, and two-photon absorption sensing methods are conducted using the same set of reference solutions so that the analytic sensitivity of each of these sensing methods may be compared with each other, as well as to slab waveguide techniques.

EXAMPLE 3

Comparison between Singly Resonant and Doubly Resonant Optical Cavities

Two approaches may be used to demonstrate enhanced sensitivity detection of doubly resonant optical cavities over singly resonant cavities: 1) operation at reduced temperatures, and 2) utilization of dyes that are not strongly broadened.

In the first case, the fluorescence yield of Cy5 is measured versus temperature down to 77° K. As the temperature is lowered, the number of occupied phonon levels is reduced, causing narrowing of the inhomogeneous linewidth.

The second approach uses a different class of dyes. For example, B-phycoerythrin has an emission peak at 575 nm with spectral width of about 20 nm. The broad absorption peak is centered about 546 nm (which can still be accessed efficiently by a doubled Nd:YAG laser at 532 nm), such that the expected enhancement factor is about 2, assuming that double resonance is obtained at 575 nm and 532 nm with FSR 42 nm and that all the fluorescence couples into a cavity mode—it is expected that less than half of the fluorescence will couple into the cavity. However, the absorption and emission spectra overlap such that fluorescence into the cavity is reabsorbed by the fluorescent tag.

This "photon recycling" effect of doubly resonant optical cavities may provide a larger enhancement of the fluorescence yield than that predicted by the enhanced spontaneous emission considerations alone.

EXAMPLE 4

Sensitivity Obtainable when Fluorescence Sensing is Employed

Due to problems arising from non-specific binding and the fact that mass sensing is not as sensitive as fluorescence sensing (especially for small molecules), fluorescence studies are also performed. In this assay, the analyte is fluorescently labeled with a Cy5 fluorescent tag. The evanescent field of the cavity optical mode induces fluorescence from the fluorescent tag, where the high Q of the cylindrical cavity leads to an effective path length much greater than the circumference of the cylindrical cavity. Picomolar sensitivity is possible using detection of fluorescence emitted upward from the broad area of the cavity cladding (i.e., the capture substrate). Since the area of the substantially planar surface of a microfabricated cylindrical cavity of the present invention is on the order of 0.001 mm$^2$ or less, the sensitivity per area is significantly larger than for a conventional slab waveguide of comparable sensitivity.

These studies are performed using labeled oligonucleotides, anti-T3, that are labeled at the 5' end with Cy5, as would be produced during the PCR process using initiation primers labeled at the 5' end. Cy5 has a high figure of merit (i.e., absorption coefficient times fluorescence quantum yield), and has peak absorption accessible by inexpensive laser diodes that emit excitation radiation of about 649 nm. The fluorescence peak is in the red at 670 nm.

Fluorescence emitted from the top of the device (so-called "side" emission in the literature) is imaged onto a low-noise photoreceiver. The sensitivity of the receiver is defined as the minimum average received power needed to obtain a signal-to-noise ratio of unity. Received power is a function of the imaging optics, the optical energy stored within the cavity, and the analyte affinity concentration. Again, the sensitivity per unit area is determined and compared with measurements made using a planar slab waveguide. If necessary, additional cavity optimization is performed to increase the sensitivity over the cavity surface area to the pM regime.

The response of this sensing mechanism to non-specific binding must also be determined. In this case, the hybridization rate is measured for the non-specific binding as mentioned for mass sensing, and for the additional situation of mismatched bases. These results do not differ from those of a slab waveguide. Again, high throughput with excellent sensitivity is achieved.

EXAMPLE 5

High Throughput Screening

While it is possible to place a 500×500 array of microfabricated cylindrical cavities onto a 1 cm$^2$ area substrate (with 10 μm diameter cavities), initially a 4×5 array is fabricated to demonstrate the capability for high throughput clinical screening applications. The reduced array size is used to simplify fabrication and the heterogeneous patterning of capture substrates and to reduce the number of labeled oligonucleotides that are required.

For simplicity, initial studies using 4×5 cavity arrays are performed with homogeneous monolayer patterning. This means that the complementary, synthetic oligonucleotide solution hybridizes at the surface of each cylindrical cavity.

The next step is heterogeneous patterning. The model system chosen for these studies, HIV-1, has tremendous clinical relevance. HIV-1 is known to have about 18 subtypes, or genotypes, which can clearly demonstrate the potential of the microcavity array technology. Synthetic, oligonucleotide capture substrates that are complementary to each of these 18 genotypes are patterned, by "stamping", onto the substantially planar surfaces of the cylindrical cavities. Stamping employs an array of micropipettes to deposit capture substrates.

The substantially planar surfaces of two of the cylindrical cavities are patterned only with neutravidin. These two cavities serve as references and will indicate non-specific binding rates.

The surfaces of the cylindrical cavities are then exposed to a sample analyte solution that includes a known combination and concentrations of the 18 synthetic oligonucleotides.

The fluorescence emissions at the surfaces of each of the cylindrical cavities are measured substantially simultaneously using a CCD array to determine the uniformity in response. If the response is highly nonuniform, the optical distribution network is redesigned.

Again, this example illustrates the individual hybridization rates, estimates the viral load, and demonstrates that high sensitivity detection can still be performed in the presence of multiple non-specific binding processes.

EXAMPLE 6

Development of Bulk Cylindrical Cavities

Bulk cylindrical cavities incorporating teachings of the present invention, such as that described previously herein with reference to FIG. 3, may be tested and refined by resonantly coupling electromagnetic radiation emitted from a narrow-line tunable laser diode into the bulk cylindrical cavity via a transmission port (e.g., a side-polished or an angle-polished optical fiber) mounted on a precision multi-axis stage. Thus, the laser line may be swept so as to trace out the resonances such that the central frequencies and Q values obtained with each laser position may be measured. In addition, a reflection port (e.g., a second polished fiber) will be used during these measurements, such that data from the transmission and reflection ports will facilitate comparison with theory. As the reflection port will reduce the Q of the cylindrical cavity, or the internal cavity power, and thus, the quantum efficiency of the cylindrical cavity, use of the reflection port may be omitted during biosensing studies.

For a bulk cylindrical cavity having a diameter of about 5 mm, the FSR between azimuthal modes at a wavelength of excitation radiation of 0.5 µm is about 13 GHz, while for a Q of $10^6$, the resonance linewidth is 600 MHz. These values are well within the tuning range and long-term frequency stability of commercial tunable laser diodes. Due to the large number of radial modes (many 1000's) for cylindrical cavity of this size (i.e., a diameter of about 5 mm), individual modes may not be resolvable due to strong overlapping of the resonance linewidths. As both the frequency and azimuthal momentum of a mode must be matched for efficient excitation, the polish of the coupling fiber will determine which modes can be observed. Detailed comparisons will be made with theory to control which modes are excited, which is an important issue as high Q modes with large areal coverage (1>>0) are desired for fluorescence biosensing. It is expected that, with optimizations, cylindrical cavities having Q's of about $10^6$ and large surface area resonance can be obtained.

EXAMPLE 7

Immunoassay with Bulk Cavities

A capture substrate comprising a monoclonal antibody monolayer specific for E. coli O157:H7 will be physically adsorbed onto the substantially planar sensing surface of the bulk cylindrical cavity. This capture substrate monolayer is not expected to significantly disturb the resonances of the cylindrical cavity, but additional measurements will be taken to verify this prediction.

The analyte (i.e. E. coli O157:H7) is prepared in solution with a concentration of $C_n$, where n is the trial number, and will specifically bind with the capture substrate.

Following hybridization of the capture substrate and the analyte, a fluorophore is introduced using a (Cy5-labeled) monoclonal tracer antibody, which specifically binds to E. coli O157:H7. Cy5 is an indicator dye with an absorption peak at 649 nm, and is commonly used as a fluorescent label. Up to $10^6$ tracer antibodies may bind to a bacterium, which is one advantage of immunoassay with multivalent antigens over molecular diagnostic assay, which requires polymerase chain reaction (PCR) to label and amplify a single DNA strand, in that fluorescence detection of a single bound bacterium may be possible. Fluorescence emission from the top of the cavity will be imaged onto a low-noise photodetector, with signal strength proportional to bound analyte concentration and optical excitation power.

The parameter of ultimate interest in these studies, and the parameter for which comparisons can be made, is the concentration of the analyte in solution, which is proportional to the concentration of analyte bound by the capture substrate.

The use of resonant optical cavities in accordance with the present invention can achieve array sizes comparable with biochips, while maintaining high sensitivity per sensing zone so as to facilitate the detection of low concentrations of analytes. It is believed that the inventive resonant optical cavities have a sensitivity of about 10 times or greater sensitivity than that obtainable with planar slab waveguides having substantially the same surface areas.

The resonant optical cavities of the present invention also have the important capabilities of real-time (for hybridization dynamics), parallel (for high throughput) readout capability of waveguide sensors.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A biosensor, comprising a resonant optical cavity with a circular cross section and a substantially planar, circular end surface, the resonant optical cavity also having a quality factor of at least about $10^4$.

2. The biosensor of claim 1, wherein the resonant optical cavity is part of an array of resonant optical cavities.

3. The biosensor of claim 1, further comprising a transmission port adjacent a surface of said at least one resonant optical cavity and configured to transmit electromagnetic radiation into said at least one resonant optical cavity.

4. The biosensor of claim 1, further comprising at least one capture substrate immobilized on or adjacent to a surface of said resonant optical cavity.

5. The biosensor of claim 4, comprising a plurality of types of capture substrates immobilized on or adjacent to said surface.

6. The biosensor of claim 5, wherein said plurality of types of capture substrates are immobilized on or adjacent to different regions of said surface.

7. The biosensor of claim 4, further comprising a sensor configured to detect binding of said at least one capture substrate with analyte or a molecule that competes with said analyte.

8. The biosensor of claim 4, further comprising a sensor for detecting at least one mass and fluorescence.

9. A biosensor, comprising a resonant optical cavity having a quality factor of at least about $10^7$.

10. A biosensor comprising a resonant cavity having a transmission port adjacent a surface of said resonant optical cavity and configured to transmit electromagnetic radiation into said resonant optical cavity wherein said transmission port comprises a waveguide distribution network configured to transmit electromagnetic radiation into a plurality of resonant optical cavities, said waveguide distribution network including at least one of a bus network and a combination tree-buss network.

11. A biosensor, comprising a resonant optical cavity, said resonant optical cavity being a doubly resonant.

12. A biosensor, comprising a resonant optical cavity, said resonant optical cavity being capable of generating whispering gallery modes and comprising at lease one of a microfabricated resonant optical cavity and a bulk resonant optical cavity, and further comprising:
 a source of electromagnetic radiation;
 a transmission port in communication with said source and disposed adjacent a surface of said resonant optical cavity so as to transmit electromagnetic radiation into said resonant optical cavity;
 at least one capture substrate immobilized on or adjacent to a substantially defect free surface of said resonant optical cavity; and
 a sensor configured to detect at least one of a mass of molecules immobilized relative to said surface and fluorescence from molecules immobilized relative to said surface.

13. A method for detecting at least one analyte in a sample, comprising:
 applying the sample to a surface of a resonant optical cavity having a quality factor of at least about $10^4$ so as to expose at least one capture substrate immobilized relative to said surface to the at least one analyte;
 introducing electromagnetic radiation into said resonant optical cavity; and
 detecting binding of the at least one analyte to said at least one capture substrate.

14. A method for detecting at least one analyte in a sample, comprising:
 applying the sample to a surface of a resonant optical cavity so as to expose at least one capture substrate immobilized relative to said surface to the at least one analyte;
 applying to at least one of a fluorescently labeled analyte and a fluorescently labeled molecule that competes with the at least one analyte for a binding site on said at least one capture substrate to said surface;
 introducing electromagnetic radiation into said resonant optical cavity; and
 detecting binding of the at least one analyte to said at least one capture substrate.

15. The method of claim 14, wherein said detecting comprises detecting excitation of fluorescent tags by employing at least one of one-photon absorption and two-photon absorption.

16. A method for detecting at least one analyte in a sample comprising:
 applying the sample to a surface of a resonant optical cavity so as to expose at least one capture substrate immobilized relative to said surface to the at least one analyte;
 introducing electromagnetic radiation into said resonant optical cavity; and
 detecting binding of the at least one analyte to said at least one capture substrate, further comprising photo-recycling said electromagnetic radiation by double resonance of sand resonant optical cavity.

17. A method for detecting at least one analyte in a sample, comprising:
 applying the sample to a surface of a resonant optical cavity so as to expose at least one capture substrate immobilized relative to said surface to the at least one analyte;
 introducing electromagnetic radiation into said resonant optical cavity; and
 detecting binding of the at least one analyte to said at least one capture substrate, wherein said detecting comprises mass sensing.

18. The method of claim 17, wherein said mass sensing comprises measuring a refractive index through cavity detuning.

19. A method for detecting at least one analyte in a sample, comprising:
 applying the sample to a surface of a resonant optical cavity so as to expose at least one capture substrate immobilized relative to said surface to the at least one analyte;
 introducing electromagnetic radiation into said resonant optical cavity; and
 detecting binding of the at least one analyte to said at least one capture substrate, wherein said detecting is effected with a concentration of the at least one analyte being at least one of nanomolar or lower and picomolar or lower.

20. A method for fabricating a resonant optical cavity, comprising:
 providing a substrate;
 fabricating a contrasting layer on said substrate; and
 forming a resonant optical cavity over said contrasting layer, said resonant optical cavity having a refractive index of at least about 1.5 times a refractive index of said contrasting layer.

21. The method of claim 20, wherein said providing said substrate comprises providing at least one of glass, quartz, and a semiconductive material.

22. The method of claim 20, wherein said forming said resonant optical cavity comprises;
 forming a material layer comprising at least one of silicon oxide and silicon oxynitride over said contrasting layer; and
 patterning said material layer to form at least one cylindrical resonant optical cavity therefrom.

* * * * *

UNITED STATES PATENT AND TRADEMARK OFFICE
CERTIFICATE OF CORRECTION

PATENT NO. : 7,384,797 B1
APPLICATION NO. : 10/089497
DATED : June 10, 2008
INVENTOR(S) : Steven M. Blair It is certified that error appears in the above-identified patent and that said Letters Patent is hereby corrected as shown below:

At Column 16, lines 42-45, please make the following changes to Equation (1) (shown below):

$$P_{cavity} = \frac{v_g \tau^2}{\pi R \tau_c} P_{inc}$$

$$P_{trans} = (1 - 2\tau/\tau_c)^1 P_{inc}$$

(a) in the second part of the equation, the exponent should be 2 rather than 1, (b) in the second part of the equation, $\tau_c$ should be $\tau_e$.

At Column 16, line 52, please make the following change to the equation (shown below):

(a) in the equation $1/\tau_c = 1/\tau_d + 1//\tau_l$, $\tau_c$ should be $\tau_e$.

At Column 17, lines 28-31, please make the following changes to Equation (4) (shown below):

(a) please remove the top part of the equation $$\frac{+72 = 1 - e^{-+60L} \approx +60L}{wg}$$

from the total equation $$\frac{+72 = 1 - e^{-+60L} \approx +60L}{wg}$$

$$n_{wg} = 1 - e^{aL} = aL$$

UNITED STATES PATENT AND TRADEMARK OFFICE
CERTIFICATE OF CORRECTION

PATENT NO. : 7,384,797 B1
APPLICATION NO. : 10/089497
DATED : June 10, 2008
INVENTOR(S) : Steven M. Blair It is certified that error appears in the above-identified patent and that said Letters Patent is hereby corrected as shown below:

so that only the bottom part of the equation remains.

$$n_{wg} = 1 - e^{aL} = aL$$

Signed and Sealed this

Fourteenth Day of October, 2008

JON W. DUDAS
*Director of the United States Patent and Trademark Office*